United States Patent [19]

Rembaum

[11] 4,267,234
[45] May 12, 1981

[54] POLYGLUTARALDEHYDE SYNTHESIS AND PROTEIN BONDING SUBSTRATES

[75] Inventor: Alan Rembaum, Altadena, Calif.

[73] Assignee: California Institute of Technology, Pasadena, Calif.

[21] Appl. No.: 21,989

[22] Filed: Mar. 19, 1979

Related U.S. Application Data

[63] Continuation-in-part of Ser. No. 887,825, Mar. 17, 1978, abandoned.

[51] Int. Cl.$^3$ ............................................... B32B 5/16
[52] U.S. Cl. .................................. 428/403; 252/62.54; 424/12; 424/32; 427/127; 428/406; 428/407; 428/524; 528/263; 528/270
[58] Field of Search ............... 528/270, 263; 428/406, 428/407, 524, 403; 252/62.54; 427/127; 424/32, 12

[56] References Cited

U.S. PATENT DOCUMENTS

| | | | |
|---|---|---|---|
| 2,702,823 | 2/1955 | Smith et al. | 528/245 |
| 3,372,086 | 3/1968 | Westfall et al. | 528/245 |
| 3,398,125 | 7/1968 | Moyer | 528/245 |
| 3,475,359 | 10/1969 | Cummings | 528/245 |
| 3,957,741 | 5/1976 | Rembaum et al. | 526/312 |
| 4,035,316 | 7/1977 | Yen et al. | 526/312 |
| 4,070,246 | 1/1978 | Kennedy et al. | 252/62.54 |

Primary Examiner—George F. Lesmes
Assistant Examiner—E. Rollins Buffalow
Attorney, Agent, or Firm—Marvin E. Jacobs

[57] ABSTRACT

Polyglutaraldehyde (PGL) is polymerized in aqueous base or in aqueous highly polar solvent basic media to prepare powders, castable films or coatings for substrates such as amine substituted microbeads. PGL microspheres can be prepared by suspension polymerization in presence of a surfactant or by precipitating PGL from solution containing surfactant. Magnetic PGL microspheres are formed by suspension polymerization in the presence of magnetic particles such as iron oxide. Polyglutaraldehyde can be converted to a fluorescent polymer by reaction with m-aminophenol or other reagent. Proteins can be readily covalently bound to the polyglutaraldehyde.

16 Claims, 9 Drawing Figures

POLYGLUTARALDEHYDE SYNTHESIS AND PROTEIN BONDING SUBSTRATES

ORIGIN OF THE INVENTION

The invention described herein was made in the course of work under a grant from the Department of Health, Education and Welfare.

CROSS-REFERENCE TO RELATED APPLICATION

This application is a continuation-in-part of Ser. No. 887,825 filed Mar. 17, 1978 now abandoned.

BACKGROUND OF THE INVENTION

1. Field of the Invention

The present invention relates to the synthesis of polyglutaraldehyde, the conversion of the polymer to a fluorescent form, the binding of proteins to the polymer and the use of the polymer-protein conjugates in biological and chemical research and testing.

2. Description of the Prior Art

The isolation and characterization of cell membranes and their components is essential for an understanding of the role in which surface membranes play in regulating a wide variety of biological and immunological activities. The present techniques used for this purpose are not quite satisfactory.

Knowledge of the nature, number and distribution of specific receptors on cell surfaces is of central importance for an understanding of the molecular basis underlying such biological phenomena as cell-cell recognition in development, cell communication and regulation by hormones and chemical transmitters, and differences in normal and tumor cell surfaces. In previous studies, the localization of antigens and carbohydrate residues on the surface of cells, notably red blood cells and lymphocytes, has been determined by bonding antibodies or lectins to such macromolecules as ferritin, hemocyanin or peroxidase which have served as markers for transmission electron microscopy. With advances in high resolution scanning electron microscopy (SEM), however, the topographical distribution of molecular receptors on the surfaces of cell and tissue specimens can be readily determined by similar histochemical techniques using newly developed markers resolvable by SEM.

Recently commercially available polystyrene latex particles have been utilized as immunologic markers for use in the SEM technique. The surface of such polystyrene particles is hydrophobic and hence certain types of macromolecules such as antibodies are absorbed on the surface under carefully controlled conditions. However, such particles stick non-specifically to many surfaces and molecules and this seriously limits their broad application.

The preparation of small, stable spherical Poly-Hema particles which are biocompatible, i.e., do not interact nonspecifically with cells or other biological components and which contain functional groups to which specific proteins and other biochemical molecules can be covalently bonded is disclosed in U.S. Pat. No. 3,957,741.

Smaller, more evenly shaped acrylic microspheres are disclosed in U.S. Pat. No. 4,138,383. Microspheres having a density differing from that of cell membranes are disclosed in U.S. Pat. No. 4,035,316 and fluorescent-acrylic copolymer microspheres are disclosed in Ser. No. 718,104 filed Aug. 27, 1976.

The hydroxyl groups can be activated by cyanogen bromide for covalent bonding of proteins and other chemicals containing amino groups to the polymeric bead. Methacrylic acid residues which impart a negative charge onto the particles are likely to prevent non-specific binding to cell surfaces and to provide carboxyl groups to which a variety of biochemical molecules can be covalently bonded using the carbodiimide method.

The derivatization procedure is unnecessarily complex and requires an additional step to prepare the bead surface for covalently binding to proteins such as antibodies, lectins and the like or other molecules such as DNA, hormones and the like. Therefore, the method of derivatization of acrylic microbeads is tedious and availability is limited. Monomeric glutaraldehyde has been used as a biochemical reagent to covalently bond proteins such as immunoglobulins to ferritin polymeric microspheres and other small particles which were then applied to map receptors on cell membranes. However, the reaction mechanism of proteins with glutaraldehyde is difficult to ascertain since its structure is still not clear and it has been reported to be in equilibrium with cyclic and hydrated forms. The reaction is difficult to carry out and frequently gives unsatisfactory results.

SUMMARY OF THE INVENTION

Direct protein bonding polyglutaraldehyde (PGL) is provided in accordance with the invention. In contrast to monomeric glutaraldehyde, the polymer contains conjugated aldehyde groups. This imparts stability to the Schiff's bases formed after reaction with proteins and, further, since the hydrophilic polyglutaraldehyde has relativey long chains extending from the surface into the surrounding aqueous medium, the heterogenous reaction with protein is facilitated.

Polyglutaraldehyde can be prepared in solution suitable for casting into film or for coating surfaces of substrates such as polymeric microbeads, particularly amine or hydrazide substituted beads. Polyglutaraldehyde microspheres can be directly prepared by suspension polymerization in presence of surfactant or by precipitation from solution containing surfactant. Polyglutaraldehyde can be converted to a fluorescent polymer by reaction with non-fluorescent reagents such as m-aminophenol. Magnetic, high density or electron dense microspheres can be prepared by coating metal particles or by suspension polymerization of glutaraldehyde in presence of a suspension of finely divided metal or metal oxide. Yields and molecular weight are increased by use of aqueous-highly polar solvent mixtures.

These and many other attendant advantages of the invention will become readily apparent as the invention becomes better understood by reference to the following detailed description when considered in conjunction with the accompanying drawings.

DESCRIPTION OF THE PREFERRED EMBODIMENTS

Figure 1:
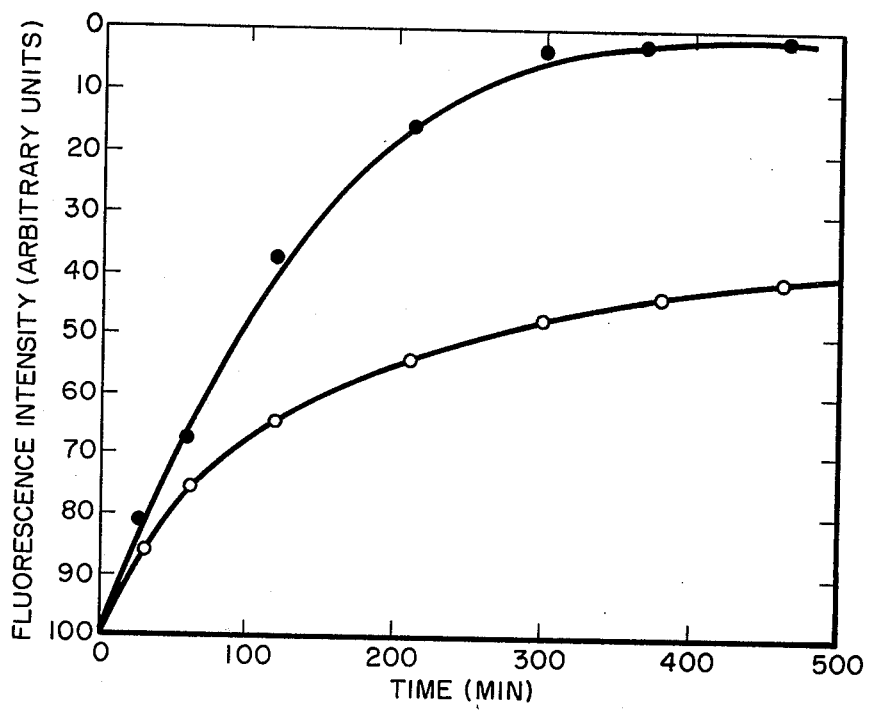
FIG. 1 shows the rate of reaction of polyglutaraldehyde (60 mg) with human IgG (4.5 mg) in PBS (50 cc) at 22° C.
- ph 6, O ph 7.4.

Polyglutaraldehyde is prepared from aqueous solution containing 5% to 50% by weight of monomeric glutaraldehyde by raising the pH of the solution above 7 preferably from 9 to 12. A spontaneous exothermic reaction proceeds in absence of catalyst. The solution is preferably cooled to a temperature of 15° C. to 30° C. for the initial polymerization period to 0.5 to 3 hours and then heated to a temperature above 40° C. until completion. The polymer is believed to contain the following repeating structure:

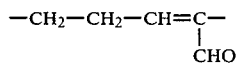

Analysis by UV or IR spectroscopy confirms the presence of conjugated aldehyde functional groups in the polymer which form more stable bonds with amino-containing molecules such as proteins.

The polymer precipitates out when the aqueous media contains at least 80% water and can be recovered by filtration and washing with water and drying. Further washing with solvents such as acetone appears to decrease yield. The polymer can be redissolved in polar solvents such as methanol, ethanol or tetrahydrofuran and especially in highly polar solvents such as dimethyl sulfoxide (DMSO) or dimethyl formamide (DMF). Solution polymerization in mixtures of water and polar solvents containing 20% to 80% solvent provides higher yields of polymer. The solution can be used for casting of films or coating of substrates. The polymer can be precipitated from solution by increasing the water content to above 80% to recover particles.

EXAMPLE 1

Polymerization: Commercial aqueous solutions of glutaraldehyde were purified by means of activated carbon and were free of polymer (absence of absorption at 235 nm, Cary 14 spectrophotometer). A 25% solution of glutaraldehyde was polymerized at 22° C. by adjusting the pH to 11.5 with NaOH. At the end of two hours, the mixture was stirred for 8 hours at 50° C. The precipitated polymer was filtered, washed with water, then acetone and dried in vacuum for 24 hours (Yield, 60%). The molar extinction coefficient $\epsilon_{235}$ measured in ethanol was found to be equal to $1.53 \times 10^3$ 1 mole$^{-1}$cm$^{-1}$. The molar extinction coefficient of glutaraldehyde at 280 nm, $\epsilon_{285}$ (extracted from aqueous solutions with ether and dried with magnesium perchlorate) was found to be equal to 4.2 1 mole$^{-1}$ cm$^{-1}$. The polyglutaraldehyde polymer was soluble in dimethyl sulfoxide and the weight average molecular weight as determined by gel permeation chromatography was found to be approximately 20,000.

EXAMPLE 2

Example 1 was repeated in 50/50 H$_2$O/DMSO media. The polymer remained in solution.

Polyglutaraldehyde exhibits a small amount of fluroescence. However, reaction of polyglutaraldehyde with specific reagents that are not in themselves fluorescent, results in a fluorescent polymer by forming fluorescent chromophores attached to the polymer. Anthrone reacts with acrolein units to form a benzanthrone fluorogen and m-aminophenol reacts with the acrolein structure to form the fluorogen, 7-hydoxyquinoline. Aminofluorescein also reacts with polyglutaraldehyde to form a fluorescent polymer.

EXAMPLE 3

50 mg of the polyglutaraldehyde from Example 1 was dissolved in 10 cc of DMSO. 20 mg of meta-aminophenol and 1 drop 10 N HCl were added and the solution was heated to 50° C. for 1 hour. The solution was highly fluorescent when irradiated with an UV lamp. Water was added to precipitate the polymer which was washed in water and dried. The isolated polymer was redissolved in DMSO and its fluorescence studied. A highly fluorescent polymer was observed with fluorescence emission maximum at 470–480 nm.

EXAMPLE 4

About 0.1 gram of the solid polymer prepared as above in Example 1 was suspended in 0.5 N sodium bicarbonate solution, and an aqueous solution of 9-aminoacridine hydrochloride (2 mg) added at room temperature. After exhaustive washing with water, an intensive fluorescence was exhibited by the polyglutaraldehyde particles under a suitable UV light source. The fluorescence did not decrease in intensity during subsequent multiple washings.

Solutions of polyglutaraldehyde (PGL) generally containing 0.1 by 5% by weight of PGL in highly polar solvents can be cast into transparent films or coatings of various thicknesses, usually 0.1 to 5 mil by coating the solution onto the surface and evaporating the film. The surfaces can be planar, particulate, spherical, rod shaped, etc., and formed of inorganic or organic material. The organic material may be metal or metal compounds, particularly magnetizable materials such as iron, nickel or cobalt or oxides thereof such as magnetite, ceramic or glass spheres and the like. Organic materials are usually small polymeric spheres such as the polyhema spheres, referenced earlier.

The PGL coating may be covalently coupled to the surface of substrates which contain amino groups such as aminosilane modified glass beads such as trimethoxyisopropylaminosilane cross-linked acrylamide homopolymer or copolymer beads. The beads are preferably very small in size from 200 Å to 100 microns, generally from 500 Å to 10 microns so that specific receptor sites on a cell surface can be tagged. Vinyl pyridine or hydroxyethylmethacrylate acrylamide copolymer beads are disclosed in U.S. Pat. No. 3,957,741 and in copending application Ser. No. 780,007 filed Mar. 22, 1977 now Pat. No. 4,170,685, the disclosure of which is incorporated herein by reference. The copolymer beads generally contain at least 50% vinyl pyridine (VP) or hema, from 5 to 35% acrylamide (AM) and 0.1 to 30% of an addition polymerizable cross-linking agent such as bisacrylamide (BAM).

Adhesion of the PGL coating to the bead is further enhanced by conversion of the amino groups to hydrazide. The modification can be effected by reaction with an excess of hydrazine hydrate at a temperature of at least 40° C. followed by separation and washing.

EXAMPLE 5

A 0.1% solution of polyglutaraldehyde in tetrahydrofuran was spread on a glass substrate. After evaporation of the solvent, a transparent film, strongly bonded to the glass surface was obtained.

EXAMPLE 6

100 mg of wet, centrifuged polyvinylpyridine microspheres (0.7μ in diameter) containing 20% AM and 20% BAM were stirred at room temperature for 4 hours with 10 cc hydrazine hydrate and then heated at 50 C with stirring for 2 hours. The microspheres were then washed with water. When tested with 2,4,6-trinitrobenzene sulfonic acid they yielded a colored product indicative of hydrazide groups.

EXAMPLE 7

The hydrazide modified microspheres of Example 6 were encapsulated with polyglutaraldehyde by stirring a 10 cc suspension (25 mg/cc) of the microspheres at room temperature for 4 hours with polyglutaraldehyde prepared as in Example 1 dissolved in DMSO (25 mg in 50 cc). After centrifuging and exhaustive washing with DMSO and water the presence of aldehyde groups on the surface was confirmed by testing with a fuchsin-Schiff test reagent.

The polyglutaraldehyde coated spheres are useful in clinical diagnostic tests, affinity chromatography, immobilization of enzymes, chemical separation or removal of urea, generally in application where bonding to amine containing compounds is useful. Numerous applications will be found in the fields of biochemistry, biology and clinical chemistry.

The reactivity of polyglutaraldehyde with low molecular weight amines was investigated in a one phase (homogeneous) and two phase (heterogeneous) system. Homogeneous reactions were carried out at relatively low temperature for example, polyglutaraldehyde was reacted with methylamine and liquid anhydrous ammonia at about −40° C. for one hour. After raising the temperature and evaporation to dryness, the products were washed with water, dried in vacuo at 60° C., analyzed spectrometrically and their nitrogen content was determined. The polymer was also soluble at room temperature in higher boiling amines e.g. allylamine, butylamine, ethanolamine, hydrazine and ethylene diamine. Its reaction with these amines was carried out at 22° C. for one hour and analyzed in the same way as in the case of the low temperature reactions.

The heterogeneous reaction was carried out by suspending the polymer (120 mg) in phosphate buffered saline (PBS) solution (20 cc) of the amine (1 g) at pH of 7.3 to 7.4 and stirring in a closed container for at least 30 hours. After washing with water and drying the nitrogen content of the products was determined. Table I shows the results of elemental analysis of the products.

TABLE I

| | Nitrogen Analysis of Reaction Products of Polyglutaraldehyde with Amines | | | |
|---|---|---|---|---|
| | Homogeneous Reaction | | Heterogeneous Reaction | |
| Amine | %N Found | % of the Theor. Amt. | %N Found | % of the Theor. Amt. |
| Methylamine | 5.6 | 38.1 | | |
| Hydrazine | 14.0 | 47.4 | | |
| Ammonia | 2.9 | 16.8 | | |
| Allylamine | 5.6 | 48.6 | | |
| Butylamine | 6.5 | 63.1 | | |
| Ethanolamine* | 5.0 | 44.6 | 0.6 | 5.3 |
| Diaminoheptane | 4.6 | 31.9 | 0.5 | 3.5 |
| Hydroxylamine** | | | 7.5 | 52.1 |
| Glycine | | | 0.9 | 8.9 |

*average of two determinations
** hydroxylamine hydrochloride was used at pH 7.3 and 2.4. The nitrogen content was 7.5 and 6.6% respectively.

The theoretical amount of nitrogen was calculated on the assumption that each unit; —$CH_2$—$CH_2$—CH=C (CHO)— will bind one molecule of amine. Spectrophotometric examination revealed that in most products the absorption at 285 nm attributed to the aldehyde group was considerably reduced. Based on results with hydroxylamine the PGL polymer contains one aldehyde group per molecular weight of 160.

The examination of the results leads to the following conclusions:

Polyglutaraldehyde exhibits a high reactivity towards low molecular weight amines under mild experimental conditions (Table I). The remarkable reactivity of hydroxylamine indicates that it may constitute a superior reagent to glycine which was used in the experiments for the inactivation of aldehyde groups on glutaraldehyde or polyglutaraldehyde activated reagents for cell labeling. The highest theoretical yields of reaction products, based on the assumption that the repeating unit in the polymer is a substituted acrolein moiety, amounted to about 50–60%. Spectrophotometric studies showed presence of unreacted aldehyde functions in the reaction products. Therefore it is likely that Schiff base formation reached an equilibrium stage and by changing the experimental conditions higher yields than those recorded in Table I may be expected.

Reactions with human immunoglobulins: Fluorescent human IgG and goat antihuman IgM (Meloy) were purified on DEAE cellulose columns. Their fluorescence intensity at different pH's was measured at room temperature by means of an Aminco Fluorimeter model SPF125.

The extent of reaction was determined by measuring the fluorescence of the supernatant after centrifugation of suspensions containing fluorescent IgG and insoluble polyglutaraldehyde. Two series of experiments were performed. In the first series, powdered polyglutaraldehyde was reacted directly with fluorescent IgG and the decrease of fluorescence measured after reaction, yielded the amount of IgG bound to the polymer. Polyhema microspheres were reacted under identical conditions and served as control.

The second series of experiments consisted of reactions with polyglutaraldehyde covalently bound to hydrazide groups on the surface of beads 0.7 in diameter.

The rate of chemical binding was studied out in the following way: PVP hydrazide beads (25 mg) were stirred with polyglutaraldehyde (25 mg) dissolved in dimethylsulfoxide (DMSO), 50 ml) for not less than 5 hours. After centrifugation and washing with DMSO and water, fluorescent immunoglobulins were added to the beads (5 cc) (Tables II, III and IV). The mixture was stirred at a controlled temperature and the loss of fluorescence with time was determined using centrifuged aliquots.

Reaction with hemoglobin: Polyglutaraldehyde or PVP polyglutaraldehyde microspheres were suspended in hemoglobin (2× crystallized, from Calbiochem) dissolved in 0.01 M phosphate buffer. The pH was adjusted with sodium phosphate and the optical density at 412 nm of centrifuged aliquots was recorded with time.

Labeling of lymphocytes with immunomicrospheres: Human lymphocytes were separated from red blood cells (rbc) by means of a Ficoll-Hypaque gradient freed from monocytes by means of iron particles and suspended in a medium at pH 7.2–7.4 to which 20% of fetal calf serum (FCS) was added. The medium (RPMI/H) consisted of RPMI 1640 (Gibco) + 0.025 M Hepes (N-2-hydroxyethyl-piperazine-N-2-ethane sulfonic acid from Calbiochem).

Microspheres to which immunoglobulins were found by means of polyglutaraldehyde (0.5 cc of microsphere suspension containing 0.5 mg of microspheres in PBS buffer at pH 7.4) were incubated for 1 hour at 4° C. with $5 \times 10^6$ lymphocytes in RPMI/H buffer (1 cc) containing 0.1% sodium azide. After addition of fetal calf serum (1.5 cc) + 0.1% sodium azide, the suspension was centrifuged at 1500 rpm (515 g). The recovered cells were resuspended in 50% RPMI/H and 50% FCS containing 0.1% sodium azide and recentrifuged. It was found necessary to repeat this washing procedure three times in order to remove practically all unbound microspheres. After the third centrifugation the cells were resuspended in RPMI/H containing 1% bovine serum albumin (BSA) and 0.1% sodium azide. The labeled cells were then counted under the microscope.

In the control experiments the lymphocytes were incubated with aggregated IgG (one hour). The aggregated IgG was prepared by dissolving human IgG (50 mg/cc) in PBS at pH 7.4 and heating the solution at 63° C. for 30 minutes. The clear supernatant layer was used to incubate cells prior to labeling.

RESULTS

Reaction of polyglutaraldehyde with low molecular weight amines: Preliminary information was obtained on the reactivity of the polymer with amino groups by carrying out the reactions with a series of amines. Table I shows the results of elemental analysis of the products. The theoretical amount of nitrogen was calculated on the assumption that each unit;

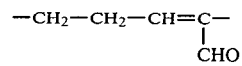

will bind one molecule of amine, In the case of hydroxylamine hydrochloride, hydrazine and butylamine the extent of reaction was of the order of 50 to 60% of the theoretical amount. (Table 1)

Reaction of polyglutaraldehyde and polyglutaraldehyde derivatized microspheres with immunoglobulins: Table II shows the amount of IgG bound to polyglutaraldehyde after stirring the suspensions of the polymer for 2.25 hours at room temperature. A constant amount of fluorescent IgG was used in these experiments.

TABLE II

| Reaction of Powdered Polyglutaraldehyde with Human IgG. (1 mg of fluorescent IgG in 10 cc of phosphate buffer, pH 7.4) | | | |
|---|---|---|---|
| Polyglutaraldehyde mg/cc | Polyhema mg/cc | Bound IgG/Polymer W/W | |
| | | ph 7.4 | pH 6.0 |
| 0.2 | — | 0.160 | 0.200 |
| 2.0 | — | 0.030 | 0.040 |
| 20.0 | — | 0.004 | 0.006 |
| | 0.2 | 0 | 0 |
| | 2.0 | 0 | 0 |
| | 20.0 | 0 | 0 |

It is obvious (Table II) that increased amounts of polymer resulted in a lower IgG/polymer ratio. The same result was obtained with microspheres derivatized with either the polymer or monomer (Table III).

TABLE III

| Comparison of the Reactivity of Glutaraldehyde and Polyglutaraldehyde Derivatized Beads. Effect of Mono and Polyglutaraldehyde Concentration (0.5 mg of fluorescent IgG in 10 cc of phosphate buffer, pH 7.4) | | | |
|---|---|---|---|
| Control* mg/cc | Polyglutaraldehyde* mg/cc | Glutaraldehyde* mg/cc | Bound IgG/Polymer W/W × 10³ |
| | 2.5 | | 11.0 |
| | 7.5 | | 4.0 |
| | 20.0 | | 1.4 |
| | | 2.5 | 6.0 |
| | | 7.5 | 2.0 |
| | | 20.0 | 0.7 |
| 2.5 | | | 0 |

*25 mg/cc of beads used in all experiments.

TABLE IV

| Comparison of the Reactivity of Glutaraldehyde and Polyglutaraldehyde Derivatized Beads. (Effect of IgG Concentration) | | | | |
|---|---|---|---|---|
| Control* mg/cc | Polyglutaraldehyde* mg/cc | Glutaraldehyde mg/cc | Human IgG mg/cc | Bound IgG Polymer W/W × 10³ |
| | 2.5 | — | 0.025 | 5.7 |
| | 2.5 | — | 0.050 | 9.5 |
| | 2.5 | — | 0.100 | 14.0 |
| | | 2.5 | 0.025 | 5.3 |
| | | 2.5 | 0.050 | 4.5 |
| | | 2.5 | 0.100 | 9.1 |
| 2.5 | | | | 0 |

Figure 2:
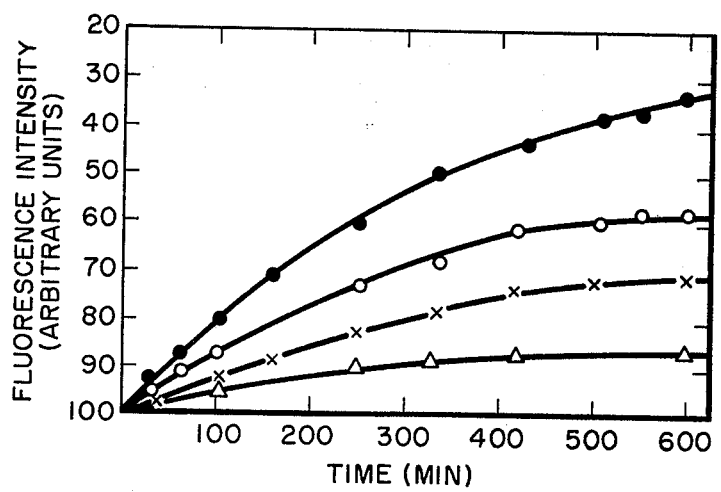
FIG. 2 shows the rate of reaction of PVP beads with fluorescent human IgG at 22° C. and ph 7.4.
- polyglutaraldehyde bound to PVP hydrazide beads ○ monoglutaraldehyde bound to PVP hydrazide beads
X PVP hydrazide beads (control)
Δ IgG in PBS (control)
Figure 3:
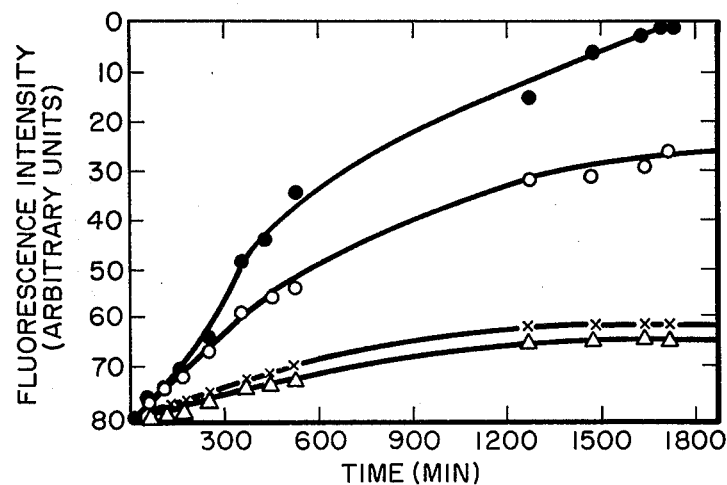
FIG. 3 shows the rate of reaction of PVP beads with fluorescent human IgG at 4° C.
● polyglutaraldehyde bound to PVP hydrazide beads
○ monoglutaraldehyde bound to PVP hydrazide beads
X PVP hydrazide beads (control)
Δ IgG in PBS (control)
Figure 4:
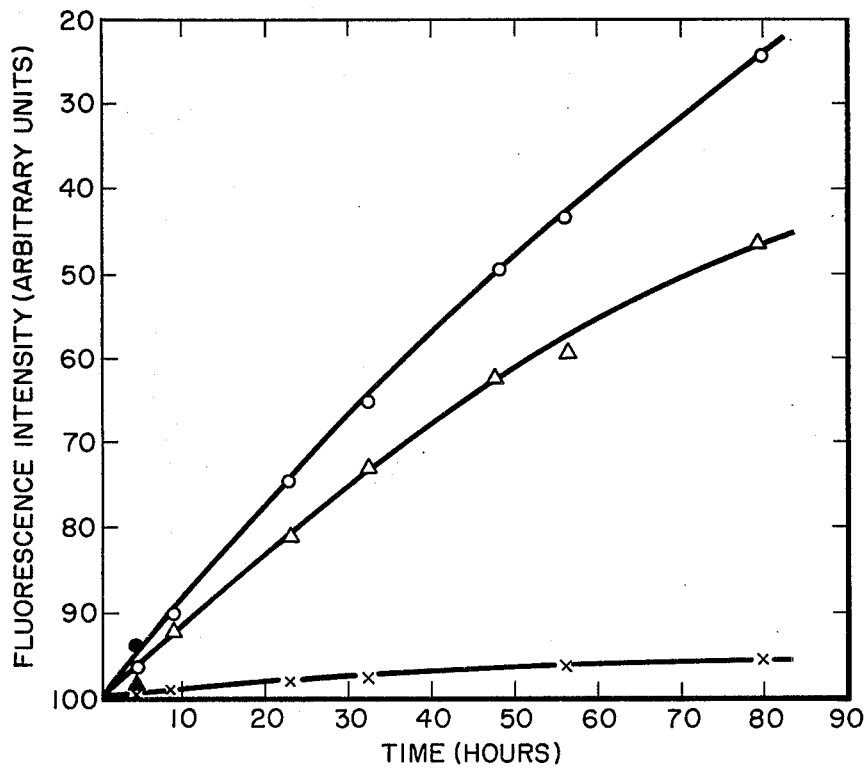
FIG. 4 shows the rate of reaction of PVP beads with fluorescent goat×human IgM at 4° C. and pH 7.4.
○ polyglutaraldehyde bound to PVP beads
Δ monoglutaraldehyde bound to PVP beads
X PVP hydrazide beads (control)

Table II indicated that larger amounts of IgG are bound to the polymer at pH 6 than at pH 7.4. This pH effect was confirmed in subsequent studies. It is also apparent that larger amounts of IgG become bound to polyglutaraldehyde than to the polyglutaraldehyde derivatized microspheres at a given reaction time (Table II and III). The decreased amount of bound IgG with increased concentration of polyglutaraldehyde is probably due to incomplete reaction and/or insufficient amount of immunoglobulins. Table II and III also prove that at a given pH considerably larger amounts of human IgG are covalently bound by means of the polymer than by means of the monomer. Information on the necessary reaction time was obtained through kinetic experiments. In FIG. 1, the decrease of fluorescence of the supernatant is plotted against time. It is obvious that at pH 7.4 the reaction is incomplete after 2.25 hours (the time used in previous experiments). Furthermore, at lower pH than 7.4, the reaction time is faster. FIGS. 2 and 3 confirm the faster reaction time of the polymer over the monomer and also show the effect of temperature. Similar results were obtained with fluorescent goat antihuman IgM (FIG. 4).

Figure 6:
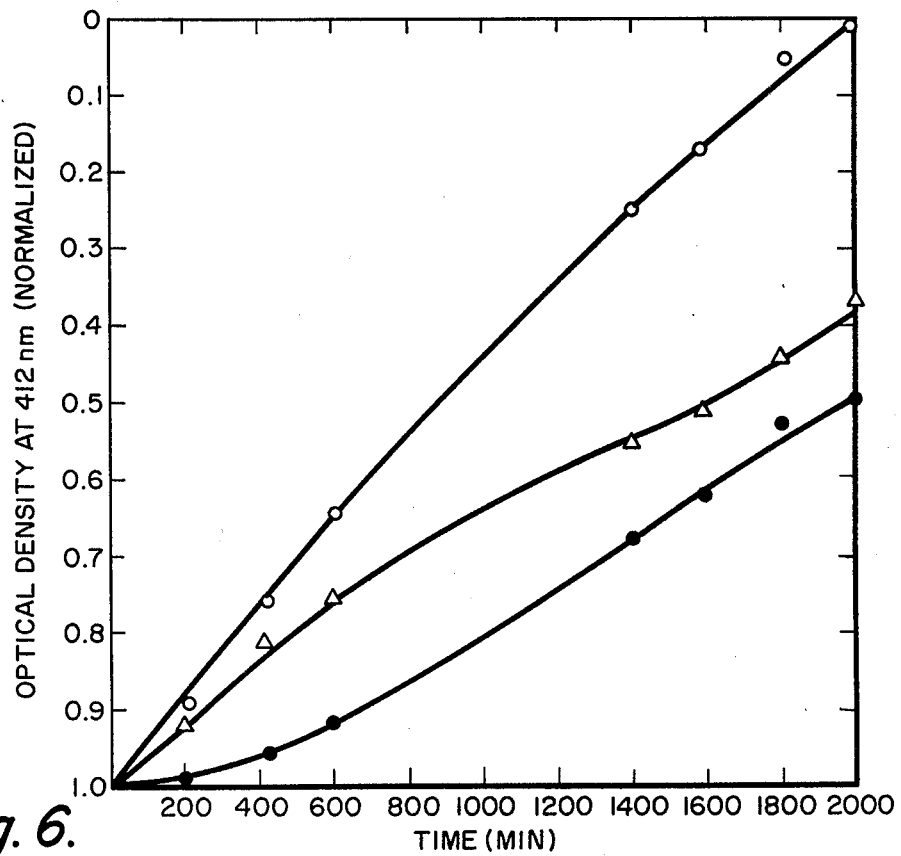
FIG. 6 shows the rate of reaction of PVP beads with hemoglobin at pH 6 and 22° C.
○ derivatized with polyglutaraldehyde
Δ derivatized with monoglutaraldehyde
⊙ polyhema (control)

Reactions with hemoglobin: Because hemoglobin has a high extinction coefficient at 412 nm ($\epsilon_{mM}=125$ based on a molecular weight of 17,000) it is a convenient model for studies of protein immobilization. It can be calculated from the absorption peak at 412 nm that at pH 6, 7.4 and 8.4 that the polyglutaraldehyde immobilized 8.8, 6.6 and 2.8% of hemoglobin respectively after 8.3 hours of reaction time. In control experiments (polyhema) the hemoglobin content was of the order of 1% based on nitrogen analysis (%N in hemoglobin used was found to be 15.2%). The hemoglobin content of the polyglutaraldehyde-hemoglobin products obtained at pH 6, 7.4 and 8.4 was calculated to be 10.4, 7.8, 5.3% respectively (based on nitrogen analysis) and agrees reasonably well with the spectrophotometric results. In contrast to the heterogeneous reaction, when polyglutaraldehyde reacted with an excess of hemoglobin homogeneously in aqueous DMSO the product was found to contain 76% of hemoglobin (nitrogen analysis). The kinetics of hemoglobin binding to polyglutaraldehyde derivatized microspheres are shown in FIG. 6. The trend of increasing reaction rate at pH 6 as compared with pH 7.4 is evident.

Figure 5:
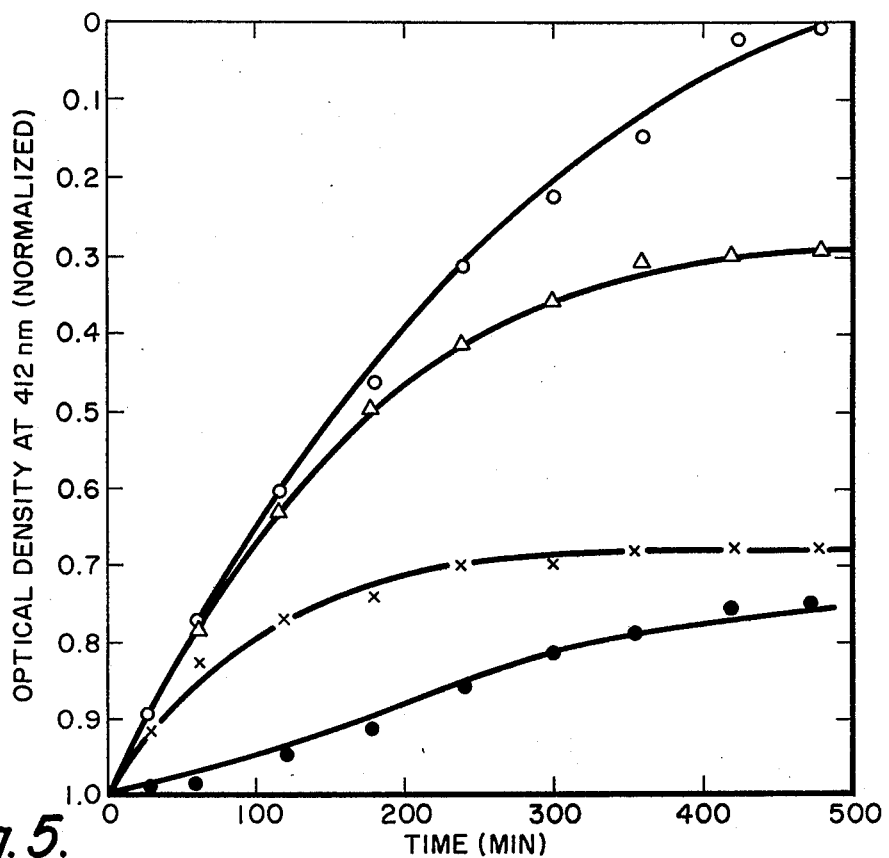
FIG. 5 shows the rate of reaction of 22° C. to polyglutaraldehyde (100 mg in 50 cc of PBS) with hemoglobin (7.5 mg) as a function of pH.
○ ph 6 Δ ph 7.4 × pH 8.4
⊙ polyhema beads, pH 6 (control)

The reactivity of the polymer with human IgG is about twice that of the monomer (Tables II, III, IV and FIGS. 2, 3, 4 and 6). The number of IgG molecules per head (0.7 in diameter) after ten hours of reaction at 22° (FIG. 2) was calculated to be equal to $3.8 \times 10^3$ and $2.3 \times 10^3$ for the polyglutaraldehyde and monoglutaraldehyde procedures, respectively. Larger amounts and faster reaction rates were observed in the reactions of immunoglobulins with polyglutaraldehyde than with microspheres (beads) derivatized with polyglutaraldehyde (compare Tables II, III and IV and FIGS. 1 and 2). The same conclusions apply to the reactions with hemoglobin (FIGS. 5 and 6).

The lowering of pH from 7.4 to 6 enchances the reaction rate. This phenomenon applies to human IgG (FIG. 1) as well as to hemoglobin (FIG. 5). To interpret this effect it is assumed that the reaction of polyglutaraldehyde takes place between free amino groups of the protein e.g. lysine residues and aldehyde groups of the polymer to form Schiffs bases. It might be expected that carbonyl addition reactions would be powerfully acid catalyzed for after attack on oxygen by a proton, the carbon atom will become considerably more positive and hence readier to react with a nucleophile:

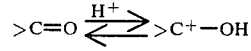

When the nucleophile is $R-NH_2$, an acid converts the amine to the unreactive species $R-^+NH_3$. It is thus expected to find that the rate of addition will show a maximum at a moderately acid pH falling off sharply at each side. This in indeed observed in practice.

The small extent of non-specific binding of immunoglobulins and hemoglobin (FIG. 2 and FIG. 5) to substrates free of glutaraldehyde and polyglutaraldehyde is attributed to physical adsorption and can be reduced by lowering the reaction temperature (FIG. 3).

The high reactivity of polyglutaraldehyde, its stability, ease of administration, and the retention of physiological activity of human immunoglobulins bound to the polymer, makes it a desirable new reagent for protein binding.

Though polyglutaraldehyde coated microspheres are more reactive than glutaraldehyde the necessity of forming a coated sphere adds unnecessary complexity of the derivitization procedure.

It has further been discovered that suspension polymerization of glutaraldehyde in presence of an emulsifying agent yields water-insoluble, polyglutaraldehyde (PGL) microspheres having a diameter from 200 Å to 10μ, usually from 500 Å to 1.5μ. Polymerization in presence of a suspension of magnetic particles results in the formation of magnetic microspheres. PGL microspheres can also be formed by precipitating PGL from a solution containing surfactant. Fluorescent microspheres can be formed by post-polymerization reaction with a fluorochrome or by polymerization in the presence of a fluorochrome.

The size of the PGL immunomicrospheres if affected by pH, concentration of surfactant and concentration of glutaraldehyde monomer. The immunomicrospheres are prepared by forming a suspension of 0.1% to 20% by weight glutaraldehyde, 0.1 to 3% surfactant in aqueous media, adjusting the pH from 7 to 13, preferably 9–12 and stirring for several hours. PGL microspheres, are then separated and washed. The aqueous media may contain 5% to 50% by weight of immiscible organic liquids such as aromatic or aliphatic organic solvents, suitably benzene, toluene, hexane, heptane, octane or triglycerides such as cotton seed oil, corn oil or soybean oil.

Microspheres containing electron-dense metals provide higher spatial resolution of cell surface features. PGL immunomicrospheres containing electron-dense metals provide more stable lables than gold particles with physically absorbed antibodies that are presently used for cell labeling. The metal containing microspheres can be synthesized by, in situ, polymerization of the PGL microspheres in presence of a suspension of finely-divided metal particles or compounds of the metal, preferably a colloidal dispersion of the metal. The metal is incorporated into the microsphere in an effective amount of from 0.5% to 20% by weight, generally from 1% to 10% by weight.

The metal or metal compound particles are preferably fine, evenly sized materials having a uniform diameter smaller than the resultant microsphere diameter, typically below 1000 Å, generally from 25 Å to 500 Å. The metals are preferably the electron=dense heavy metals having a high atomic number above 50, preferably above 75 such as Pb, Ni, Co, Pt, Au, Fe. The metal may be magnetically attractable such as Fe, Ni, Co or alloys thereof or an inorganic magnetic compound such as a metal oxide. The magnetic material is preferably a magnetic iron oxide of the formula $Fe_3O_4$. Some hard, ceramic type ferrites, such as lithium ferrites can also be used. The metal or compound can be made into a readily dispersible form by suspension in water containing a surfactant such as polyethylene imine.

The PGL microspheres can be rendered fluorescent by reaction with compounds that form fluorogens with acrolein such as anthrone and m-aminophenol or with aldehyde reactive fluorochromes such as aminofluorescein, 9-amino acridine, propidium bromide or fluorescein isothiocyanate (FITC). Highly florescent microspheres can also be prepared by suspension polymerization of glutaraldehyde in presence of fluorochromes containing amino groups.

The surfactants are water soluble, nonionic, cationic or anionic materials, generally organic which is defined to include fluorocarbon and hydrofluorocarbon and silicon compounds. Cationic surfactants can be amines, amine salts, sulfonium, phosphonium or quarternary ammonium compounds. The surfactants may be utilized alone or in presence of 1 to 5% by weight of a suspending agent such as a polyethylene oxide, glycerine, polyacrylamide or a polyethylene imine. Representative cationic surfactant is Guar C13 (Stein and Hall Specialty Chem.) which is a cationic guar gum. Water-soluble, anionic surfactants can be selected from the commercially available carboxylic acids, sulfuric esters and aklane sulfonic acids, for example, sodium dodecyl sulfate or Zonyl FSP which is an anionic substituted fluorocarbon.

Nonionic surfactants are usually the polyethylene oxide and/or polypropylene oxide derivatives of phenol, alcohols or fatty acids. Preferred non-ionic surfactants are water-soluble copolymers having molecular weights from 800 to 10,000 of acrylamide with 30–60% by weight of acrylic esters or alkyl- or alkoxy-methyl acrylamides such as isobutoxymethacrylamide as disclosed in U.S Pat. No. 4,098,987.

EXAMPLE 8

To a 5% (w/z) aqueous glutaraldehyde solution (100 cc) containing 1% (w/v) of Aerosol 604 surfactant (American Cyanamid Co.-copolymer of 60% acrylamide-40% isobutoxymethacrylamide), 10 N NaOH was added dropwise until a pH of 11 was reached. The mixture was then deaerated with nitrogen, the contain tightly closed and placed on a mechanical shaker for 24 hours at room temperature. After 1, 2 and 4 hours of reaction time the pH was adjusted to 11 by addition of 10 N NaOH. The mixture was subsequently extensively dialyzed against water and then centrifuged three times at 2000 G (30 min.). The PGL spheres (yield: 200 mg) of an average diameter of 2000 Å±200 as determined by scanning electron microscopy, could be redispersed in 0.01 M, pH 7.4 phosphate buffer saline (PBS) or distilled water. By varying the concentration of surfactant, monomer or pH the size of microspheres could be altered in a predictable way.

Figure 7:
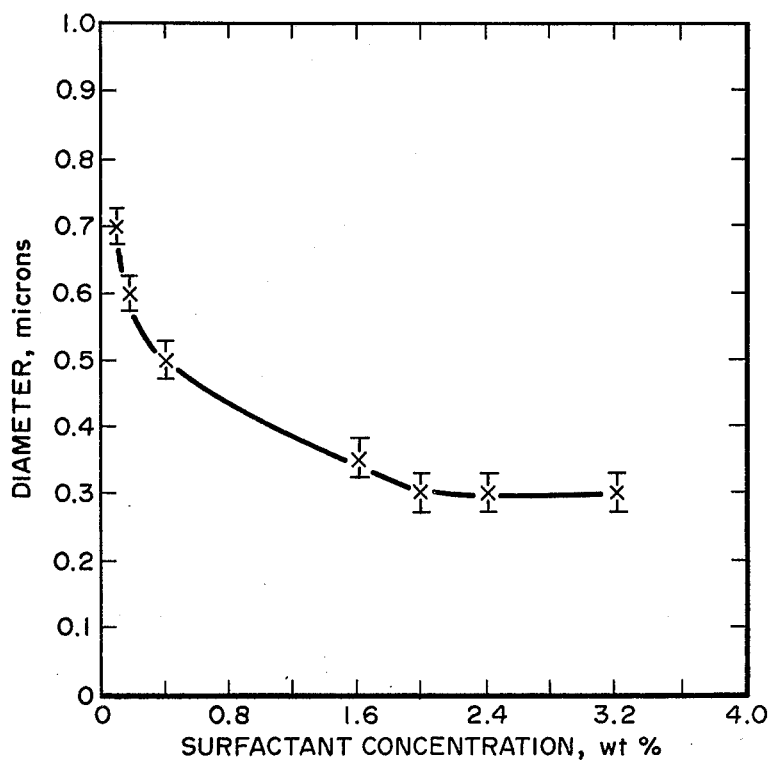
FIG. 7 is a graph showing the effect of surfactant concentration on microsphere diameter (10 wt. % glutaraldehyde, pH 11)
Figure 8:
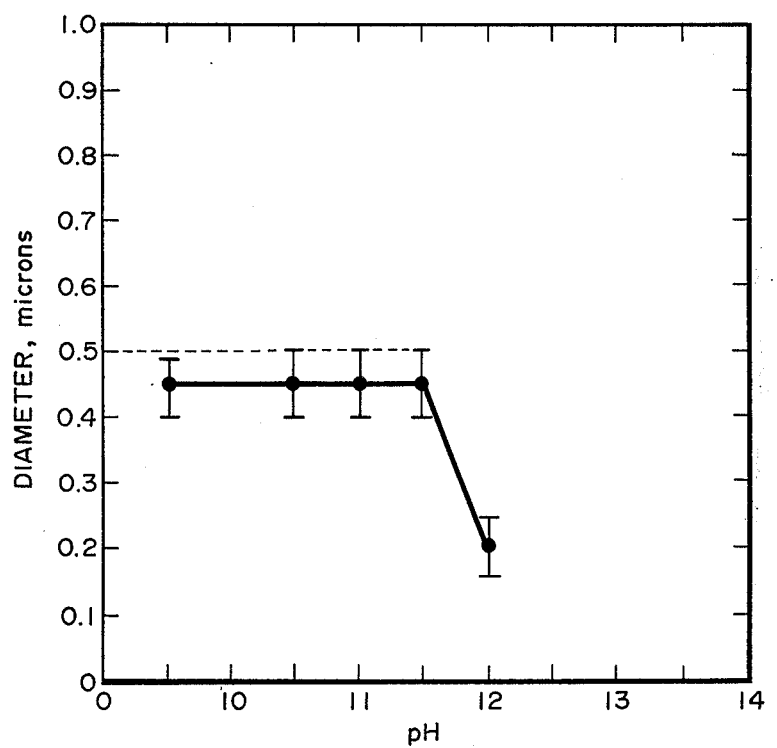
FIG. 8 is a graph showing the effect of pH on microsphere diameter (10 wt. % glutaraldehyde, 1 wt. % surfactant)
Figure 9:
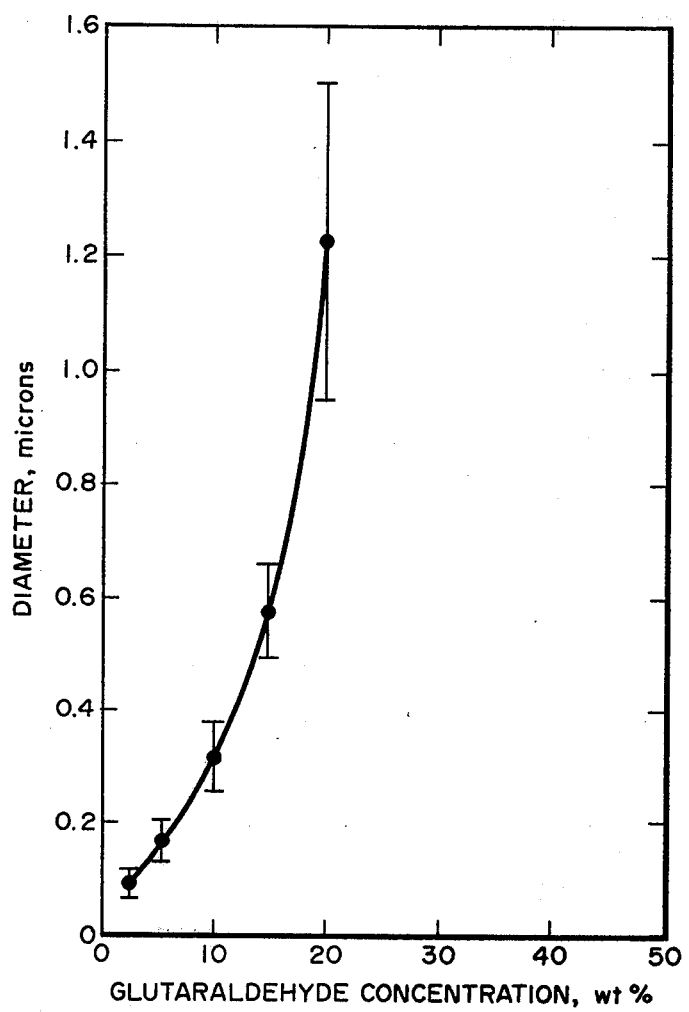
FIG. 9 is a graph showing the effect of glutaraldehyde concentration on microsphere diameter (1 wt. % surfactant, pH 11).

The procedure of Example 8 was repeated varying concentration of surfactant and monomer and pH to determine the effect on microsphere diameter as shown in FIGS. 7, 8 and 9. In the absence of surfactant, monoglutaraldehyde undergoes an aldol condensation reaction at pH 7 very slowly. The rate of polymerization increases at pH>7 to yield a powdery product containing aldehyde groups. In the presence of surfactants and in basic aqueous solution PGL precipitates out in the form of spherical colloidal particles. The decrease in size with increased pH is most probably due to the occurrence of a Cannizaro reaction which results in the formation of carboxyl groups. This is evidenced by the increased solubility with increased pH and increased neutralization equivalent of isolated PGL microspheres prepared at several pH's (Table V). The diameter of microspheres also decreases with decrease of monomer or surfactant concentration.

TABLE V

SYNTHESIS OF PGL POWDER AND MICROSPHERES (0.2μ IN DIAMETER) AS A FUNCTION OF pH, POTENTIOMETRIC TITRATION WITH 0.1 NaOH (in aq. DIMETHYL FORMAMIDE (1:1)

| PGL Powder pH | Micro- Spheres pH | Meg. Carboxyl g. PGL | No. of Carboxyl Groups per g. × $10^{-19}$ | per micro. × $10^{-7}$ |
|---|---|---|---|---|
| 10.0 |  | <0.023 | <2.0 |  |
| 11.0 |  | 0.05 | 3.0 |  |
| 11.5 |  | 0.10 | 6.0 |  |
| 12.3 |  | 0.13 | 7.8 |  |
| 13.5* |  | 0.95 | 50.0 |  |
|  | 10.5 | <0.03 |  | <1.5 |
|  | 11.5 | 0.10 |  | 24.0 |
|  | 12.3 | 0.30 |  | 75.0 |

*Soluble polymer, precipitated at pH 6.

The presence of aldehyde groups was ascertained by means of Fourier. Transform Infra Red absorption (FTIR) spectra reaction with hydroxylamine hydrochloride and with 2.4-dinitrophenyl hydrazine. The absorption bands at 1720, 1680 and 1635 $cm^{-1}$ were previously attributed to vibrations of non-conjugated, conjugated aldehyde groups and of carbon carbon double bonds in the α position to the aldehyde function, respectively.

It is evident from FTIR Spectra that all the absorption bands which characterize the PGL powder are also present in PGL mon magnetic and magnetic microspheres. An additional absorption at 1540 $cm^{-1}$ is probably due to a residual component of Aerosol 604. The presence of iron oxide core in the magnetic PGL microspheres causes shifts of some absorption wavelengths (e.g., 1680, 1360 and 1125 $cm^{-1}$). The assignment of 1680 $cm^{-1}$ absorption band to an aldehyde function was confirmed by reaction of PGL with sodium bisulfite. The reaction product of PGL with sodium bisulfite had no absorption at 1680 $cm^{-1}$. Additional evidence for aldehyde functions was provided by the nitrogen analysis of PGL powder, non magnetic and magnetic microspheres reacted with hydroxylamine hydrochloride. The results of the nitrogen analysis recorded in Table VI show that the number of aldehyde groups decreases as the pH at which the polymers were synthesized increases and are consistent with the gradual increase of the neutralization equivalent (Table V), i.e., with increased concentration of carboxyl groups. The latter are formed at the expense of aldehyde groups (Table V) as expected in case of the Cannizzaro reaction.

TABLE VI

Reaction of PGL Powder and PGL microspheres (0.2μ diameter) prepared at different pH with hydroxylamine. (Nitrogen analysis of reaction products.)

| PGL Powder pH | PGL Microspheres pH | % N in Reaction Product* | No. of Aldehyde Groups per g × $10^{-20}$ | No. of Aldehyde Groups per microsph. × $10^{-7}$ |
|---|---|---|---|---|
| 10.0 | | 7.8 | 3.4 | |
| 11.5 | | 7.3 | 3.1 | |
| 12.3 | | 4.3 | 1.8 | |
| 13.5 | | 2.2 | 0.9 | |
| | 10.5 | 6.7 | | 1.2 |
| | 11.2 | 6.1 | | 1.0 |
| | 11.2** | 6.7 | | 1.2 |

*corrected, % N found before reaction: powder 0.05%, microspheres, 1.8%.
**magnetic microspheres (iron content, 14%, by atomic absorption)

Qualitatively, the presence of aldehyde groups can be shown by means of 2,4-dinitrophenyl hydrazine which yields yellow-orange PGL microspheres when reacted hetrogeneously in aqueous suspension at pH 2. PVP hydrazide microspheres used as control gave negative color tests. PGL microspheres have been observed to aggregate at acidic pH and at high salt concentration. Since microsphere aggregation must be avoided during the cell labeling procedure it was necessary, in the case of magnetic PGL microspheres, to replace 0.15 M NaCl with 0.25 M sucrose in the phosphate buffer. However, nonmagnetic PGL microspheres could be safely used as a suspension in PBS.

EXAMPLE 9

The procedure of Example 8 was followed except that Aerosol 604 was replaced by 1% w/v of an anionic surfactant, Zonyl FSA (Dupont). The average diameter of the PGL microspheres was 0.1μ.

EXAMPLE 10

The procedure of Example 8 was repeated except that Aerosol 604 was replaced by a mixture of 1% w/v of a cationic surfactant, Guar C-13 and 5% w/v of a suspending agent, polyethylene oxide having a molecular weight of 100,000. The average diameter of the PGL microspheres was 0.2μ.

EXAMPLE 11

Highly fluorescent PGL microspheres were found by adding 10 N NaOH to an aqueous suspension of 1% w/v Aerosol 604 surfactant containing and 0.05% 9-amino acridine fluorochrome until a pH of 11 was reached. Thereafter aqueous glutaraldehyde was added (final concentration 5% w/v) and the pH readjusted to 11. The microspheres were purified as described in Example 8. Highly fluorescent green PGL microspheres were formed having an average diameter of 0.15μ.

The procedure of Example 11 was repeated with 0.05% w/v of various fluorochromes and gave the results presented in the following table.

TABLE VII

| Fluorochrome | fluorescene |
|---|---|
| Propidium bromide | red |
| Amino fluorescein (Isomer 1) | green |
| o-phthaldehyde | green |
| 5-dimethyl amino-1-naphthalene sulfonyl hydrazide | green |
| Fluorescein isothiocyanate (FITC) dissolved in an excess of | |

TABLE VII-continued

| Fluorochrome | fluorescene |
|---|---|
| ethylene diamine | green |

EXAMPLE 12

Highly fluorescent PGL microsphere were prepared by shaking at 25° C. for 24 hours 20 mg of PGL microspheres prepared as described in Example 8 with 1 mg of 0.01% FITC solution in ethylene diamine. The fluorescent microspheres were purified as in Example 8 and redispersed in water or PBS.

EXAMPLE 13

The addition of 2, 4-dinitrophenylhydrazine to the PGL microspheres of Example 8 at pH 2 yielded a permanent yellow color.

EXAMPLE 14

The procedure of Example 8 was repeated in the presence of 1% w/v of Ferrofluid (aqueous dispersion of $Fe_3O_4$ containing 5% w/v iron) resulted in the formation of magnetic beads having an average diameter of 0.1 microns. The purification of iron containing microspheres consisted of dialysis against water and separation from diamagnetic impurities by means of a permanent magnet. The material was finally dispersed in phosphate buffered sucrose (0.5 M). The concentration of particles in solution was based on dry weight analysis. A known volume of solution as dried at 110° C. to constant weight.

EXAMPLE 15

Dispersible iron oxide was prepared by dissolving 10 gr of ferrous chloride and 13.5 gr of ferric chloride in 210 cc of 1% w/v polyethylene imine (M.W. 1800) aqueous solution. 50% NaOH was added to pH 7. The reaction mixture was refluxed for 3 hours, dialyzed extensively against water and separated magnetically three times from non-magnetic particles. The magnetic polyethylene imine-iron oxide particles were redispersed in water and then sonicated with a clinical sonicator for 10 minutes. Magnetic particles having a diameter of 300Å with amine groups on the surface were formed.

EXAMPLE 16

1% polyethylene imine-iron oxide from Example 15 was added to the suspension polymerization system of Example 8 and resulted in the formation of magnetic PGL microspheres.

EXAMPLE 17

The addition of 0.01% FITC solution in ethylene diamine to the suspension polymerization system of Example 14 resulted in magnetic fluorescent PGL microspheres having an average diameter of 0.1μ.

EXAMPLE 18

20 mg of the magnetic PGL microspheres from Example 14 were shaken at 25° C. for 24 hours with 1 mg of FITC dissolved in 0.02 cc of distilled ethylene diamine. The highly fluorescent, magnetic, PGL microspheres were dialyzed extensively against water and then separated 3 times magnetically. The purified microspheres were redispersed in water or phosphate buffered sucrose (0.5 M).

EXAMPLE 18

PGL microspheres were formed in aqueous suspension containing immiscible solvent. 10 N NaOH was added to a stirred aqueous solution at 25° C. of 5% w/v glutaraldehyde, 10% toluene and 2% Triton X-100 until a pH of 11 was reached. The solution was stirred for 3 hours and then centrifuged at 2000 G three times. PGL microspheres having an average diameter of about $0.5\mu$ were formed and separated and washed by the procedure described in Example 8.

EXAMPLE 19

Magnetic PGL microspheres were formed by addition of 1% w/v of Ferrofluid to the suspension polymerization system of Example 18 and were separated magnetically three times and washed and dialyzed.

EXAMPLE 20

PGL microspheres were formed by dissolving 125 mg of PGL powder from Example 1 in 2.5 cc anhydrous DMSO. The solution was stirred vigorously. 50 cc of 2% aqueous polyethylene oxide (M.W. 100,000) was added and the solution stirred for another hour. PGL microspheres having an average diameter of $0.1\mu$ were formed and were purified by centrifugation (3 times) at 2000 g and redispersed in water.

EXAMPLE 21

The procedure of Example 20 was repeated except that 4% w/v of aqueous Zonyl FSA anionic surfactant was substituted for the polyethylene oxide and PGL microspheres were formed.

EXAMPLE 22

The procedure of Example 20 was repeated except that 4% aqueous Zonyl FSC cationic surfactant was substituted for the polyethylene oxide and PGL microspheres were formed.

EXAMPLE 23

Fluorescent microspheres were prepared by dissolving 125 mg of PGL powder and 12 mg of aminofluorescein in 205 cc of anhydrous DMSO with vigorous stirring. Addition of 2% aqueous polyethylene oxide (PEO) results in the formation of fluorescent PGL beads having an average diameter of $0.1\mu$.

EXAMPLE 24

The procedure of Example 20 was repeated except that 6% of the PEI-iron oxide from Example 15 was added to the DMSO solution. Fluorescent, magnetic, PGL microspheres were produced.

EXAMPLE 25

The procedure of Example 8 was repeated substituting 50 mg of water soluble polyacrylamide for the Aerosol 604 surfactant and resulted in the formation of PGL microspheres having an average diameter of $0.2\mu$.

EXAMPLE 26

When the procedure of Example 25 was repeated in presence of 1% w/v of Ferrofluid, magnetic beads were formed.

Reactions of PGL microspheres with human IgG.

In order to determine the necessary time of reaction to conjugate antibodies to PGL microspheres, the rate of reaction was investigated using fluorescent human IgG as a model. The decrease of fluorescence intensity with time is a measure of the rate of covalent building. An initial fast reaction is experienced for non-magnetic, magnetic PGL microspheres as well as for PGL in form of a powder as compared with the control run in which polyvinyl pyridine microspheres free of aldehyde groups were used. The decrease of fluorescence intensity in the control experiment indicates a physical adsorption of human IgG. The PGL powder consisted of particles of 20 to $80\mu$ in diameter, consequently had a much small area than the PGL microspheres of 2000 Å in diameter and this is probably the main reason for the lower reaction rate.

Labeled cells and magnetic separation

The marking of cell surface receptors by means of fluorescent, non-fluorescent or magnetic fluorescent PGL microspheres was found to be simple and efficient as evidenced by numerous tests using fixed human or turkey rbc as models. Preliminary experiments with live human lymphocytes to label IgG molecules on B cells were also successful.

EXAMPLE 27

Labeling of human rbc

An aqueous PGL microsphere suspension (0.2 cc, 2 mg of microspheres, diameter 2000 Å was diluted with PBS (0.6 cc) of purified goat antirabbit (0.2 mg in 0.2 cc of PBS). The mixture was gently agitated for 3 hours at 4° C. Bovine serum albumin added (20 mg) and the agitation was continued for another hour. Unbound antibody was separated by passing the suspension through a sepharose 4B column. The separation was monitored spectrophotometrically at $\lambda = 280$ nm (Cary 14).

Human rbc from a normal donor and fixed with glutaraldehyde were sensitized with rabbit antihuman rbc. The rbc ($10^7$) suspended in 0.5 cc of PBS containing the antiserum (0.2 mg) were agitated for 30 min. at room temperature and the cells were separated and washed three times by spinning the PBS suspension in an international centrifuge at 500 G. The goat antirabbit derivatized microspheres were than added to the pellet of sensitized human rbc and the mixture was gently agitated for 1 hour at 4° C. The rbc were then separated from unreacted conjugated microspheres by centrifugation (3 times at 500 G). The labeled cells were resuspended in PBS (0.4 cc) and examined in light or scanning electron microscope (SEM).

Two controls were used in each experiment: (1) microspheres were conjugated with human IgG and interacted with sensitized rbc; and (2) microspheres conjugated with goat antirabbit IgG interacted with non-sensitized rbc.

Labeling of human lymphocytes

The labeling of live human lymphocytes by means of PGL microspheres was tested.

PBL microspheres (2000 Å in diameter) were conjugated with FITC tagged human IgG as described in Example 27. The number of labeled Fc receptors was counted under the fluorescent microscope and agreed with values obtained previously within $\pm 10\%$.

The separation of magnetically labeled human rbc was achieved in the following way:

Mixtures of human rbc with the following ratios of unlabeled to labeled cells were prepared: 1:1, 7:1 and 9:1. The mixtures (10 cc) were gently stirred in a glass vial fitted with a horseshoe magnet (300 gauss). At the end of two hours, cells which were not attracted to the vessel walls were isolated. Cells attracted by the magnet were diluted with 10 cc of PBS and the magnetic separation was repeated. SEM examination showed that 95% of unlabeled cells could be thus separated from all three synthetic mixtures.

The extent of non-specific interaction with live human lymphocytes as well as the efficiency of magnetic separation of cell subpopulations by means of magnetic sorter is at present under investigation.

A new convenient immunoreagent in form of PGL microspheres was synthesized in a variety of sizes and with a relatively narrow size distribution. High intensity of fluorescence can be imparted to the PGL microspheres during the synthesis which still leaves a high concentration of aldehyde groups on the surface. The aldehyde functional groups permit covalent binding with antibodies, enzymes and other proteins in a single step. Therefore this immunoreagent eliminates the previously used intermediate steps in which the cyanogen bromide and carbodiimide reaction was used. The wide range of ionic strength and pH without occurrence of aggregation and the high specificity of the PGL microspheres, at least as far as human rbc is concerned, are also desirable properties.

A minor synthetic modification yields fluorescent magnetic PGL microspheres for a large number of potential applications.

The use of magnetic particles has created a great deal of interest in biochemical research and clinical medicine when used as supports for immobilized enzymes. Their easy retrieval from liquors containing colloids and undissolved solids should be of practical value. The separation of proteins and chemical compounds by affinity chromatography can be simplified by elimination of tedious centrifugation procedures and column chromatography steps. Magnetic particles have also recently been tested in radioimmunoassay techniques in hyperthermia treatment of cancer, in guidance of magnetic particles to a vascular malformation such as cerebral aneurism with the intent to seal the defect by inducing thrombosis.

Other proposed applications have been as tracers of blood flow or vehicles for drug delivery. The first successful application of magnetic immunomicrospheres to the separation of B and T cells has been demonstrated. These results were later confirmed using C-1300 neuroblastoma cells. There is little doubt that physical sorting of cell sub-populations has become a necessity. Many separation methods, while useful are limited by the restricted set of parameters upon which separation can be based and by the fact that they are batch techniques.

New flow cytometers and sorters permit quantitative multiparameter measurements and sorting based on these measurements, but are limited as far as the number of cells that can be separated in a given time. Magnetic cell sorters have the potential of cell separation in a continuous process. The evidence obtained in the present investigations using model cell systems indicates that magnetic PGL immunomicrospheres of desirable sizes can be conjugated with proteins in a simple and convenient manner, therefore offer a potential for large scale immunological cell sorting as well as other applications.

It is to be understood that only preferred embodiments of the invention have been described and that numerous substitutions, modifications and alterations are permissible without departing from the spirit and scope of the invention as defined in the following claims.

What is claimed is:

1. Microspheres having a diameter from 200 Å to 10μ consisting essentially of polylutaraldehyde having a repeating conjugated aldehyde containing structural unit of the formula:

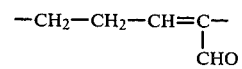

2. Micropheres according to claim 1 in which the diameter is from 500 Å to 1.5μ.

3. Microspheres according to claim 1 containing 0.5 to 40% of metal containing particles having a diameter below 1000 Å.

4. Microspheres according to claim 3 in which the metal particles have a diameter from 25 Å to 500 Å and represent in an amount from 1% to 10% by weight.

5. Microspheres according to claim 3 in which the metal has an atomic number above 50.

6. Microspheres according to claim 5 in which the particles are magnetically attractable.

7. Microspheres according to claim 6 in which the particles comprise $Fe_3O_4$.

8. Microspheres according to claim 1 in which the fluorogen groups are the reaction products of acrolein groups and a compound that forms a fluorogen on reaction with said groups.

9. Microspheres according to claim 1 containing fluorogen groups.

10. Microspheres according to claim 9 in which the fluorogen is the reaction product of aldehyde groups with an aldehyde reactive fluorochrome.

11. Microspheres according to claim 10 in which the fluorochrome is selected from aminofluorescein, 9-amino acridine, propidium bromide, or fluorescein isothiocyanate.

12. Microspheres according to claim 9 bound to protein.

13. Microspheres according to claim 12 in which the protein is selected from antibodies, antigens, immunoglobulins, lymphocytes or hemoglobin.

14. Microspheres according to claim 13 in which the protein is an antibody.

15. Microspheres according to claim 14 further comprising the fluorescent condensation product of polyglutaraldehyde and a non-fluorescent reagent.

16. Microspheres according to claim 15 in which the reagent is selected from anthrone, m-aminophenol and aminofluorescein.

* * * * *

UNITED STATES PATENT AND TRADEMARK OFFICE
CERTIFICATE OF CORRECTION

PATENT NO. : 4267234
DATED : May 12, 1981
INVENTOR(S) : Alan Rembaum

It is certified that error appears in the above-identified patent and that said Letters Patent are hereby corrected as shown below:

Column 2, line 35, correct "relatively".

Column 11, line 45, change "w/z" to --w/v--.

Column 12, line 21, change "Meg." to --Meq.--.

line 24, change "0.023" to --0.03--.

line 46, change "mon" to --non- --.

Column 18, line 14, correct "polyglutaraldehyde".

line 29, change "represent" to --are present--.

Signed and Sealed this

Twenty-ninth Day of September 1981

[SEAL]

Attest:

Attesting Officer

GERALD J. MOSSINGHOFF

Commissioner of Patents and Trademarks